(12) United States Patent
Beller

(10) Patent No.: US 10,449,309 B2
(45) Date of Patent: Oct. 22, 2019

(54) POWDER INHALER AND POWDER INHALATION SET

(71) Applicant: Klaus-Dieter Beller, Kenzingen (DE)

(72) Inventor: Klaus-Dieter Beller, Kenzingen (DE)

( * ) Notice: Subject to any disclaimer, the term of this patent is extended or adjusted under 35 U.S.C. 154(b) by 582 days.

(21) Appl. No.: 15/115,674

(22) PCT Filed: Jan. 20, 2015

(86) PCT No.: PCT/EP2015/000093
§ 371 (c)(1),
(2) Date: Jul. 31, 2016

(87) PCT Pub. No.: WO2015/113743
PCT Pub. Date: Aug. 6, 2015

(65) Prior Publication Data
US 2016/0346488 A1    Dec. 1, 2016

(30) Foreign Application Priority Data

Jan. 30, 2014  (DE) .......................... 10 2014 001 072
Apr. 17, 2014  (DE) .......................... 10 2014 005 647

(51) Int. Cl.
*A61M 15/00*   (2006.01)
*A61M 15/08*   (2006.01)
*A61M 11/00*   (2006.01)

(52) U.S. Cl.
CPC ...... *A61M 15/0041* (2014.02); *A61M 11/002* (2014.02); *A61M 15/0003* (2014.02);
(Continued)

(58) Field of Classification Search
CPC .......... A61M 11/002; A61M 2202/064; A61M 2206/14; A61M 15/00; A61M 15/0001;
(Continued)

(56) References Cited

U.S. PATENT DOCUMENTS 5,070,870 A * 12/1991 Pearce .............. A61M 15/0028
                                                  128/203.12
6,073,629 A    6/2000 Hardy
(Continued)

FOREIGN PATENT DOCUMENTS

DE    10 2005 046 644 B3   7/2006
DE    10 2005 046 645 B3   7/2006
(Continued)

*Primary Examiner* — Joseph D. Boecker
(74) *Attorney, Agent, or Firm* — Gudrun E. Huckett

(57) ABSTRACT

The invention relates to a powder inhaler and to a powder inhaler set that contains the powder inhaler. The powder inhaler comprises two half-shells (3, 4), which can be or are articulated to each other and which enclose an air inlet region, a powder deposition region and powder release region, and an outlet region in a joined arrangement, through which regions a fluid path extends. At least one of the half shells (3, 4) has at least one air inlet opening (8) in the air inlet region, and at least one air-swirling structure (5) is present in the air inlet region, which air-swirling structure defines the fluid path between the at least one air inlet opening (8) and the powder deposition and release region. Furthermore, one of the half-shells (3, 4) has at least one powder-accommodating recess (9) in the powder deposition region and powder release region, while the outlet region has at least one deagglomeration structure (17, 17') and an outlet for aerosol, which outlet is formed by the half-shells (3, 4).

18 Claims, 5 Drawing Sheets

(52) U.S. Cl.
CPC .... *A61M 15/0005* (2014.02); *A61M 15/0021* (2014.02); *A61M 15/0051* (2014.02); *A61M 15/08* (2013.01); *A61M 15/0043* (2014.02); *A61M 15/0063* (2014.02); *A61M 2202/064* (2013.01); *A61M 2205/586* (2013.01); *A61M 2206/14* (2013.01); *A61M 2207/00* (2013.01)

(58) Field of Classification Search
CPC .......... A61M 15/0003; A61M 15/0005; A61M 15/00021; A61M 15/0028; A61M 15/003; A61M 15/0033; A61M 15/0035; A61M 15/0038; A61M 15/004; A61M 15/0041; A61M 15/0043; A61M 15/0045; A61M 15/0051; A61M 15/006; A61M 15/0063; A61M 15/0086; A61M 15/08
See application file for complete search history.

(56) References Cited

U.S. PATENT DOCUMENTS

| | | | | |
|---|---|---|---|---|
| 2002/0108611 | A1* | 8/2002 | Johnston | A61M 15/0028 128/203.15 |
| 2006/0237010 | A1* | 10/2006 | De Boer | A61M 15/0045 128/203.15 |
| 2013/0074841 | A1* | 3/2013 | Von Schuckmann | A61M 15/0028 128/203.15 |
| 2014/0007875 | A1* | 1/2014 | Aberg | A61M 15/0045 128/203.15 |
| 2014/0230817 | A1* | 8/2014 | Richardson | A61M 15/0028 128/203.15 |
| 2015/0343159 | A1* | 12/2015 | Farr | A61M 15/0026 128/203.15 |
| 2016/0151589 | A1* | 6/2016 | Ohrt | A61M 15/0065 128/203.15 |
| 2016/0346490 | A1* | 12/2016 | Beller | A61M 15/08 |
| 2017/0106154 | A1* | 4/2017 | Herder | A61M 15/0028 |
| 2018/0280639 | A1* | 10/2018 | Alexander | A61M 15/0086 |

FOREIGN PATENT DOCUMENTS

| | | | | |
|---|---|---|---|---|
| DE | 10 2009 030185 A1 | 12/2010 | | |
| DE | 10 2009 041 664 A1 | 3/2011 | | |
| DE | 20 2011 103 503 U1 | 12/2011 | | |
| EP | 1 769 818 B1 | 4/2007 | | |
| EP | 2 015 812 B1 | 1/2009 | | |
| GB | 2 270 293 A | 3/1994 | | |
| GB | 2460281 A | 11/2009 | | |
| WO | WO-2008101992 A1 * | 8/2008 | ........ A61M 15/0028 |
| WO | 2011/154371 A1 | 12/2011 | | |
| WO | WO-2012004485 A2 * | 1/2012 | ........ A61M 15/0028 |
| WO | 2013/036881 A2 | 3/2013 | | |
| WO | 2014/006135 A2 | 1/2014 | | |
| WO | WO-2015110832 A1 * | 7/2015 | .......... A61M 15/003 |

* cited by examiner

POWDER INHALER AND POWDER INHALATION SET

BACKGROUND OF THE INVENTION

The invention concerns a powder inhaler and a powder inhalation set comprised of powder inhaler and blister element.

Powder inhalers for sublingual, nasal, and inhaling delivery of solid drugs or other substances in powder form are known. They can be designed as propellant gas-free delivery devices that release an aerosol due to the inspiration process, respectively, a deep inhalation process. The energy for dispersing is obtained by the inspiration flow. In this context, the substance in powder form is contained in a storage container; special storage containers such as blisters are also known. Depending on the type of powder inhaler, the pure active ingredient is used or the active ingredient together with a carrier that is an innocuous excipient, for example, lactose or glucose for adhered active ingredient particles.

Known powder applicators or powder inhalers, depending on the design, may deliver up to three different types of powder. Such a powder inhaler is disclosed in EP 1 769 818 B1. Here, a propellant gas-free powder inhaler is used for inhaling delivery of solid drugs in powder form and enables also inhalation of a powder combination. This is achieved in that the powder inhaler comprises at least two storage containers in which different powders are stored separate from each other in several dosing units. The powders can be combined correspondingly and can be delivered through a common inhalation tube.

The powder inhaler disclosed in DE 10 2005 046 645 B3 is also provided for inhalation of two different powders and comprises also at least two storage containers for the different powders and makes it possible that they can be metered separate from each other in a dosing device and subsequently can be mixed with each other during inhalation.

The delivery even of different powders can be realized as an individual dose.

In order to improve the agglomeration degree and the emptying degree of the powder upon inhalation, the powder inhaler of DE 10 2005 046 644 B3 comprises in the inflow air channel a coil-shaped or spiral-shaped swirling device in order to swirl the air prior to supply to the powder and to obtain in this way a finer distribution of the powder in the air stream.

An inhaler for individual doses is known from DE 20 2011 103503 U1. The powder inhaler for capsules described therein comprises a blade housing and a mouthpiece housing as well as a capsule carrier and several blades. The powder inhaler disclosed therein is intended to be used without complex preparation by an untrained user. The entire inhalation process is to be simply activated by a sliding movement; for this purpose, the device described therein has only two housing parts that are movable relative to each other and, due to their displacement relative to each other, initially the insertion opening for the capsule is closed and, in this way, the capsule is retained in a bore within the inhaler. In the interior of the inhaler, the capsule is then opened by suitably designed metallic blades.

EP 2 015 812 B1 discloses a powder inhaler for simultaneous delivery of several medicaments which are present in different depressions in an individual dose blister strip. For insertion of the blister, a mouthpiece of the powder inhaler is movably attached on a strip support. On the strip support of the powder inhaler, corresponding depressions for receiving the blister depressions are formed. A cover film of the inserted blister can be pulled off when the mouthpiece is closed in that the cover film is provided with a folded-over pulling tab that is projecting from the closed powder inhaler.

While most known inhalers are comprised of a plurality of components, which makes manufacture very expensive and complex, the above-mentioned inhaler of DE 20 2011 103503 U1 is already of a constructively simple design and can be manufactured inexpensively, but requires the use of blades and provides only a short simple transport path in order to transfer the powder from the capsule by means of inhaled air into a corresponding aerosol.

Based on this prior art, it is the object of the present invention to provide an inhaler that can be produced even more simply and remains hygienically safe even for multiple uses.

SUMMARY OF THE INVENTION

This object is solved with a powder inhaler comprising:
two half shells that are connectable or connected to each other in an articulated manner and in a joined arrangement enclose an air inlet area, a powder deposition and release area, and an outlet area through which a fluid path is extending, wherein
in the air inlet area at least one of the half shells comprises at least one air inlet opening and at least one air swirling structure is present which defines the fluid path between the at least one air inlet opening and the powder deposition and release area,
in the powder deposition and release area, one of the half shells comprises at least one powder receiving depression, and
the outlet area comprises at least one de-agglomeration structure and an outlet for aerosol that is formed by the half shells.

Accordingly, there is the further object to provide a powder inhalation set that provides the inhaler together with active ingredient in direct ready to use form.

This object is solved by the powder inhalation set characterized in that it comprises a powder inhaler according to the invention and a blister element dimensioned for reception in the powder inhaler, wherein the blister element comprises a support film with at least one depression that is formed for receiving at least one active ingredient powder that is inhalable, and a cover plate that closes off the depression, wherein the at least one depression of the blister element in size and position is formed correspondingly for reception in the at least one powder receiving depression of the powder inhaler.

Further embodiments of the powder inhaler and of the powder inhalation set are disclosed in the dependent claims.

A powder inhaler according to the invention comprises two half shells that are connected or can be connected in an articulated manner to each other. The two half shells enclose in a joined arrangement an air inlet area, a powder deposition and release area, and an outlet area through which a fluid path is extending. In the air inlet area, at least one of the half shells comprises one or several air inlet opening(s). Moreover, in the air inlet area at least one air swirling structure is present which defines the fluid path between the air inlet opening(s) and the powder deposition and release area where at least one of the two half shells comprises at least one powder receiving depression. By means of the air swirling structure the air in the air inlet area is swirled so that by means of the swirled air stream, supplied to the powder deposition and release area, the powder is completely conveyed out of the powder receiving depression and already becomes at least partially de-agglomerated. In the outlet area, both half shells are formed to an outlet that comprises at least one de-agglomeration structure. In this way, the two half shells in the joined state form quasi a flow housing for the fluid path between the air inlet openings and the outlet so that the aerosol, which is formed upon inhalation in the powder deposition and release area from the powder to be inhaled, provided in the powder receiving depression, and from breathed-in air, can be inhaled through the outlet by the user. The outlet of the powder inhaler can be designed as a mouthpiece, for example, formed as a spout, or for inhalation through the nose as a nose piece, for example as a curved nose tube.

Advantageously, due to the articulated arrangement, only two components are required for joining the two half shells to the powder inhaler, without further components being required. The half shells of the powder inhaler can thus be manufactured advantageously as injection-molded components which makes manufacture particularly inexpensive. Due to the articulated connection of the half shells, the powder inhaler can be opened and closed in a simple way which simplifies keeping clean the powder inhaler in case of multiple uses. Moreover, the hinges assist in correct joining of the half shells by the user.

In order to be able to handle the powder inhaler properly and in order to be able to carry it along everywhere, it is advantageously comprised of two flat half shells with an elongate base that is substantially rectangular, possibly also trapezoidal or drop-shaped or oval. The shell is formed due to the rectangular or differently shaped base being rimmed by a wall or wall sections. The elongate half shells have therefore a longitudinal axis and its two ends comprise, on the one hand, the air inlet openings and, on the other hand, the outlet. Thus, the air inlet openings are arranged at a wall section that is facing away from the outlet side of one or both half shells; advantageously, this is the half shell that does not carry the powder receiving depression. The reason for this is that the fluid path shaped for an optimal flow course is to be formed by means of the overall design.

"Fluid path" means in this context the path that is traveled first by the air alone and, after the entrainment of the powder by the air, by the aerosol. The aerosol is created when the portioned active ingredient in powder form that is present in the depression is entrained by inhaled air and is sufficiently mixed and dispersed along the following diffusor stretch. In order to form an ideal channel, preferably a venturi tube like channel, in which the fluid path is localized, at least one of the half shells, preferably however both of them, comprise at least two guide webs which are extending all the way to the powder receptacle from the wall section where the air inlet openings are provided and/or from both lateral wall sections adjoining next to the air inlet openings. In this context, the guide webs of one half shell, relative to their height, extend all the way to the other half shell or, when both half shells comprise guide webs, all the way to the guide webs of the other half shell so that two side by side neighboring guide webs form an air supply channel that comprises a cross-section that tapers toward the powder receiving depression and delimits the fluid path in the air inlet area.

The air is compressed in a funnel shape by the cross-sectional tapering and is caused to rotate due to the air swirling structure arranged in the air channel and forming flow obstacles for the air stream flowing along the fluid path so that the air stream generated by inhalation has a highest speed and turbulence at the "funnel tip" when it reaches the powder receiving depression. The latter is framed on both sides by guide walls which extend away from the outermost longitudinal webs guide the air stream out of the air inlet area through the powder receiving depression. In this way, the powder is completely carried away out of the powder receiving depression. An optimal flow course is thus ensured independent of the type and depth of inhalation of the user.

When an embodiment of the powder inhaler is provided by means of which at the same time two or more medicaments in powder form are to be inhaled and accordingly two or more powder receiving depressions are present in one of the half shells, the guide webs are arranged such that at least one air supply channel leads to each one of the powder receiving depressions, respectively.

The air swirling structure which is arranged in the air supply channel between two neighboring guide webs, i.e., in the case of several air supply channels there are also several air swirling structures, can be formed as an elliptical truncated cone having one or several coil-shaped projections extending along its wall surface. In the simplest case, this spiral-like air swirling structure can be simply inserted; preferably however, the truncated cone can be connected by means of its base surface to the wall section of one of the half shells facing away from the outlet side so that, for cleaning purposes, for example, it can be pivoted outwardly when the half shells are open. Particularly preferred, this articulated connection can be realized captively by at least one film hinge so that the air swirling structure can be produced as one piece together with one of the half shells.

As an alternative to this air swirling spiral, an air swirling structure according to the invention can also be formed by several transverse stays which extend between neighboring guide webs, wherein the transverse stays in both half shells are arranged such that they extend with opposite orientation when in the joined arrangement i.e., they do not lie on top of each other but cross each other. Due to these flow obstacles, the fluid path extends from the air inlets alternatingly in both half shells all the way to the powder receiving depression and is thus caused to rotate and is turbulent.

The articulated connection of the two half shells can be provided, for example, by a hinge on neighboring sidewalls or by a pivot joint. By means of the hinge, the half shells can be opened and closed in a folding movement about a longitudinal axis provided on the edge while the pivot joint that is preferably arranged in the area between a sidewall and the wall section that is facing away from the outlet side enables a rotation of the two half shells relative to each other. In this way, the embodiment with hinge provides that the elements in the interior of the powder inhaler, for example, the de-agglomeration structures, can project past the partition plane of the respective half shell as long as they can be accommodated in the second half shell. When a pivot joint is used, care must be taken that the respective structures do not project past the wall of the half shell.

The de-agglomeration structure or each de-agglomeration structure in the outlet area can be formed by a group of profiled elements that are arranged in a ring shape about the cylinder, wherein the cylinder as well as the profiled elements of each de-agglomeration structure extend between the two half shells. Depending on the embodiment of the articulated connection of the two half shells, the agglomeration structure(s) can be arranged on one of the two half shells or, when more than one de-agglomeration structure is present, at different locations in the outlet area of both half shells. For the configuration with pivot joint, the de-agglomeration structure(s) is/are formed by two half structures that do not project past the partition plane of the half shells and of which one half structure is arranged in each half shell, respectively, so that the half structures in the joined arrangement of the half shells form the de-agglomeration structure. The de-agglomeration structures serve as flow obstacles so that upon transport of the powder and entrainment by the air stream larger powder particles, where necessary, are broken up by the flow obstacles and are thus comminuted. Moreover, in this way, where necessary, the active ingredient can be separated from a carrier substance. Further mechanical resistance elements of any shape, respectively, flow resistance elements, can be positioned as de-agglomeration devices in order to embody the fluid path so as to be tailored as needed and matched to the specifications of the medicament. Conceivable are also in this context, for example, webs, vane-shaped or wall-shaped as well as bollard-shaped structures.

The overall configuration of the fluid path serves for optimal flow and acceleration of the inhaled air stream and for improved entrainment and dispersion of the active ingredient in powder form. In particular, it is to be achieved that the powder contained in the powder receiving depression is completely removed therefrom with one inhalation.

The free configuration of the profile of the fluid path and of the corresponding flow obstacles or de-agglomeration devices enables the adaptation of the inhaler for different active ingredients that are suitable for inspiration and that can be in particular drugs. For example, dry drugs in powder form can be dispersed in the stream as particles of defined size.

The inhaler according to the invention is particularly hygienic in regard to handling due to its design and due to the possibility of opening and cleaning it. It is without blades, springs or levers. When producing and delivering powder aerosol, the adhesion and the friction in the inhaler play an important role. Adhesion and friction between active ingredient and inhaler can be overcome by the fluid path course in order to prevent that the powder particles adhesively deposit on the inner inhaler surface. The flow obstacles in the air supply area and outlet area are designed so as to optimize the speed and turbulence in the air stream in order to achieve the best possible powder release and de-agglomeration which leads to improved inhalation performance.

In order to release an active ingredient contained in a depression of a blister element when the blister element is received with the depression in the powder receiving depression of the powder inhaler, the half shell that does not comprises the powder receiving depression(s) can be provided with a plunger at a corresponding opposite location in the powder deposition and release area. This plunger is inserted by means of an elastic insert in this half shell so as to be movable in the direction of the at least one powder receiving depression and is formed as a pricker for opening an active ingredient depression of the inserted blister element. In this way, by pressure from the exterior at the location of the elastic insert, the plunger can be moved in the direction toward the powder receiving depression(s) for puncturing the blister film and, upon release of the outer pressure, returns into its initial position as a result of the restoring force of the elastic insert.

Moreover, at one of the half shells on a sidewall section at the level of the powder receiving depression a cutout can be provided whose width and height corresponds to the width and height of a blister element that is predetermined for insertion into the powder inhaler. The powder inhaler itself can be designed correspondingly so that it serves for receiving defined blister elements.

Expediently, the cutout can have a height that is higher than the height of the blister element. Height relates in this context to the height of the blister film and not to the height of the medicament depression. Then, the second half shell, thus expediently the half shell that does not comprise the cutout, has a projection at the sidewall section which, in a joined arrangement of the half shells, is positioned above the cutout. The projection is designed to close off the cutout when an appropriate blister element is received in the powder inhaler, i.e., the blister film is projecting through the cutout out of the powder inhaler and the projection is contacting the blister film. The cutout can be provided such that the inhaler is suited for right-handed persons or for left-handed persons.

By closing off the cutout after insertion of the blister element, it is prevented that at an undesirable location air is sucked into the inhaler upon inhalation.

Moreover, the half shell that comprises the powder receiving depression can comprise at least one stop element that serves for framing a blister element that is predetermined for reception in the powder inhaler. Therefore, the blister element when inserted cannot slide.

One embodiment provides that opening of the active ingredient depression of the blister element is not realized by perforation by means of a deflection projection embodied as a movable pricker but by pulling off a cover film. The latter projects by means of a folded-over pulling tab through the cutout out of the joined powder inhaler. In order to secure the inserted blister element when pulling off the cover film, both half shells can be provided at the sidewall sections at the level of the powder receiving depression opposite the cutout and opposite the projection with a ribbing whose width corresponds to the width of a blister element which is predetermined for insertion into the powder inhaler so that the blister element is secured between the ribbed wall sections in the joined arrangement of the powder inhaler.

Alternatively, it can be provided that at the half shell that comprises the powder receptacle a projection, for example, a dome-shaped projection, is provided that is embodied to engage a corresponding recess of the blister element that is provided to be inserted into a powder inhaler according to the invention.

The projection or ribbing serves as an abutment for pulling off the cover film by means of the pulling tab that is projecting out of the closed powder inhaler so that the active ingredient depression of the blister element remains safely within the powder receiving depression.

In the area of the powder receiving depression, at least one of the two half shells can be manufactured of transparent plastic material in order to enable viewing of the interior of the powder receiving depression and to thereby permit visual inspection whether the powder has been completely removed from the powder receiving depression after an inhalation process has been completed.

On the half shells locking means for joining are provided in a suitable way; the configuration of such locking means is known to a person of skill in the art. The locking means can be provided on the appropriate edges of the half shells. Expediently, both half shells, where necessary, also connected spiral-like insertable air swirling structure, are provided with locking means so that these elements can be simply locked with each other and coupled upon folding them together.

Further subject matter of the invention is a powder inhalation set that is comprised, on the one hand, of the powder inhaler according to the invention and, on the other hand, of a corresponding blister element that is dimensioned for reception in the powder inhaler. Such a blister element comprises a support plate or support film with a depression in which the powder, respectively, the active ingredient that can be inhaled, is received. A matching blister element can also comprise two or more depressions with different active ingredient powders that are to be inhaled at the same time. The blister element comprises moreover a cover plate or cover film that closes off the depression(s) for as long as the powder is to be stored in the blisters. The depression(s) of the blister element is/are configured in regard to size and position for corresponding reception in the powder receiving depression(s) of the powder inhaler.

In order to release the powder by opening the depression of the blister element when the inhalation process is to be performed, the cover plate can be removed from the support plate and thus from the active ingredient depression in that the cover plate is formed, for example, with a foldable pulling tab which, with the blister element inserted in the powder inhaler, projects at the level of the powder receiving depression through the cutout in a sidewall section out of the powder inhaler and can be pulled off.

An alternative embodiment provides a simpler blister element that must not project with a section of the cover plate out of the powder inhaler but is only inserted with precise fit with the active ingredient depression into the powder receiving depression of the powder inhaler. Optionally, in this embodiment a capsule-like blister element or a specially designed capsule can be used also. Opening of the active ingredient depression is not realized here by pulling off the cover plate but by perforation thereof. A powder inhaler according to the invention which is designed for this is provided with a plunger that is elastically movable and embodied as a pricker opposite the powder receiving depression.

It can also be provided that a powder inhaler according to the invention is provided with both opening mechanisms so that both blister types can be opened.

Further embodiments as well as some of the advantages that are associated with these and further embodiments will become more clear and easier to understand with the aid of the following detailed description referencing the attached figures. Elements or parts thereof which are substantially identical or similar can be provided with the same reference characters. The figures are only a schematic illustration of an embodiment of the invention.

BRIEF DESCRIPTION OF THE DRAWINGS

In this context, it is shown in.

DESCRIPTION OF PREFERRED EMBODIMENTS

The device according to the invention relates to a powder inhaler for inhaling delivery through mouth or nose of an active ingredient in powder form which is stored in a blister, wherein the active ingredient may be a medicament but also an active ingredient which is not necessarily defined as a medicament and which is inhaled by a person.

Figure 1:
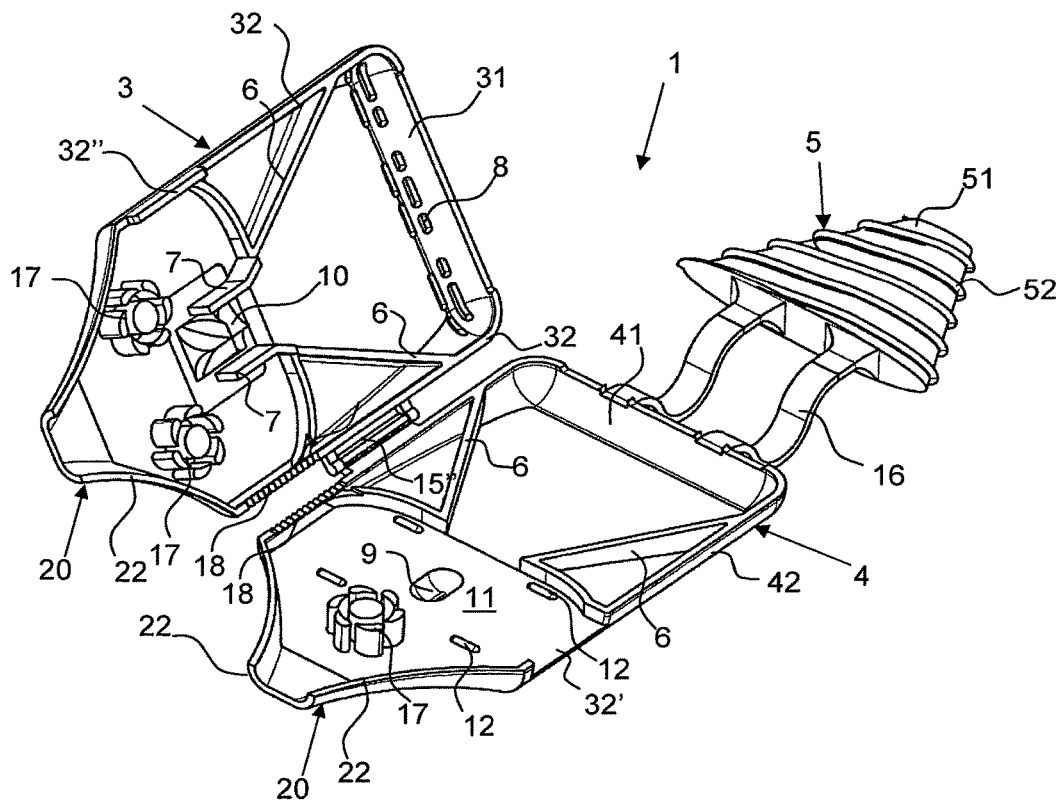
FIG. 1 a perspective view of the powder inhaler according to the invention of two half shells that are connected to each other by a hinge in open state with connected air swirling structure.
Figure 2:
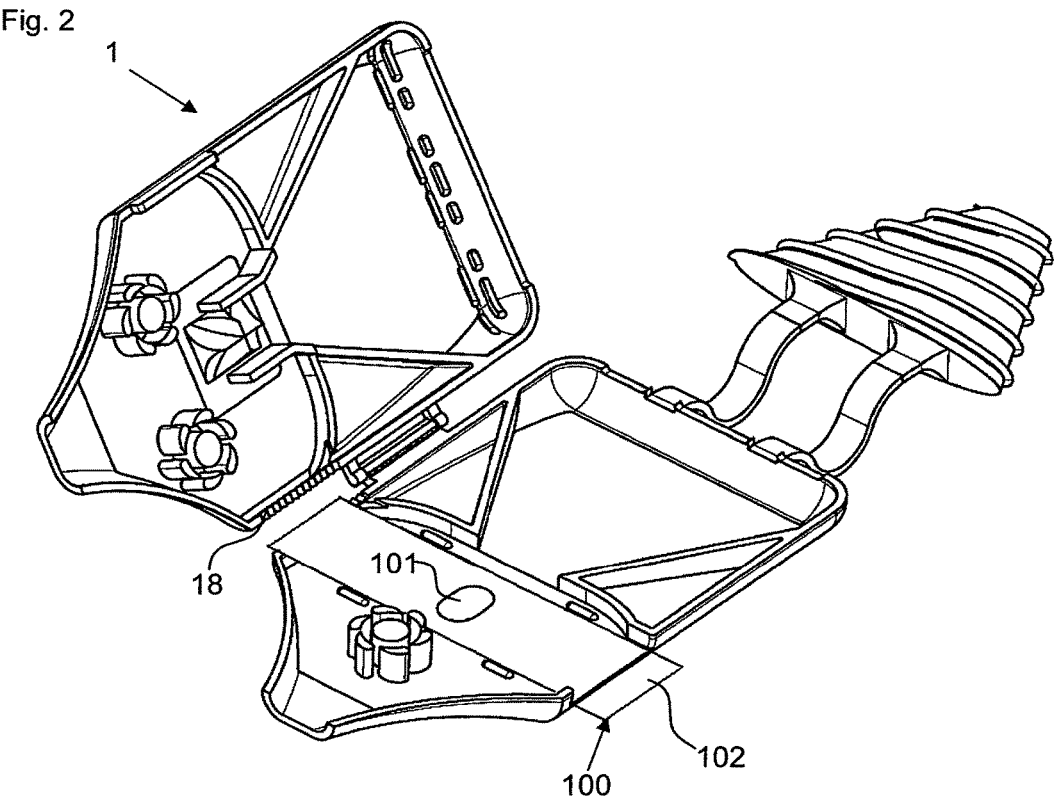
FIG. 2 a view according to FIG. 1 with inserted blister.
Figure 3:
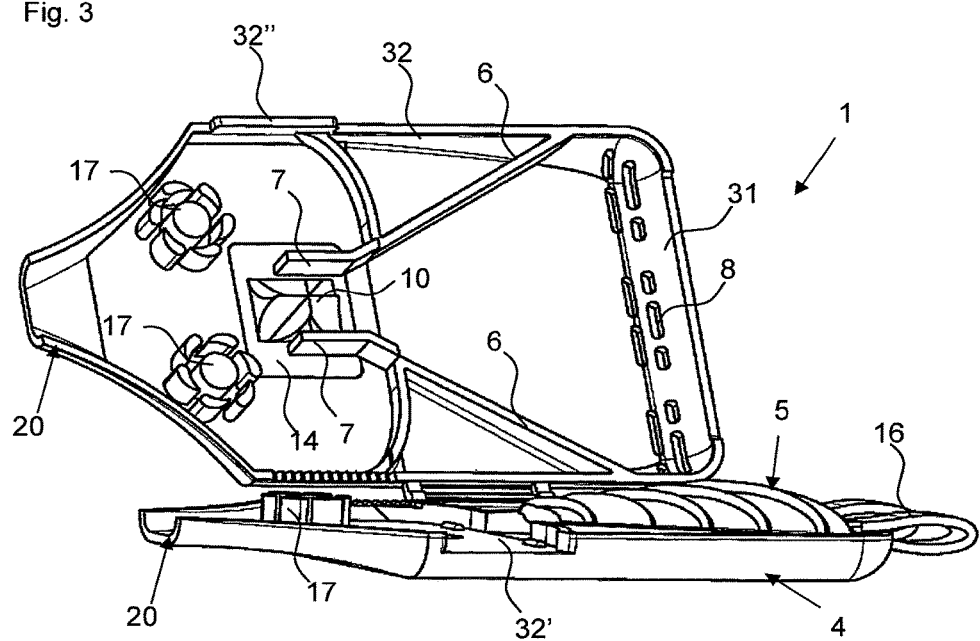
FIG. 3 a perspective view of the powder inhaler of FIG. 1 with inserted air swirling structure, FIG. 4 a longitudinal section view of the closed powder inhaler without blister.

FIG. 1 shows two half shells 3, 4 of a powder inhaler 1 according to the invention for inhaling delivery, wherein the half shells 3 and 4 are connected by a hinge 15" in an articulated manner. One of the half shells, presently the lower half shell 4, is connected by a film hinge 16 with a spiral-like air swirling structure 5 which is comprised of an elliptical truncated cone-shaped base member 51 about which a projection 52 is winding so that the air stream from the inlet openings 8 must follow the spiral 52 and therefore is caused to rotate and be turbulent. After folding the air swirling structure 5 into the space between the guide webs 6 (compare FIG. 3), the half shells 3, 4 in the folded state form the ready to use powder inhaler. In order to transfer the powder inhaler 1 into the ready to use state, the blister element 100 is inserted into a place provided for this purpose (compare FIG. 2). After folding in the air swirling structure 5 and folding closed the two half shells 3 and 4 (compare FIG. 4), the powder inhaler 1 is ready to use; only the medicament depression 101 of the blister element 100 must be opened.

FIGS. 5 to 8 show a further powder inhaler 1 according to the invention with an alternative air swirling structure 5 and a pivot joint 15, 15' as an articulated connection of the two half shells 3 and 4. In this context, the air swirling structure 5 is formed by transverse stays 53 which extend in a zigzag line between the guide webs 6 of each half shell 3, 4 so that the transverse stays 53 in the joined arrangement of the half shells 3, 4 cross each other (compare FIG. 8) and thereby guide the air stream from the air inlet openings 8 alternatingly into the lower half shell 4 and the upper half shell 3 with respective directional change so that turbulences are also generated here.

Figure 9:
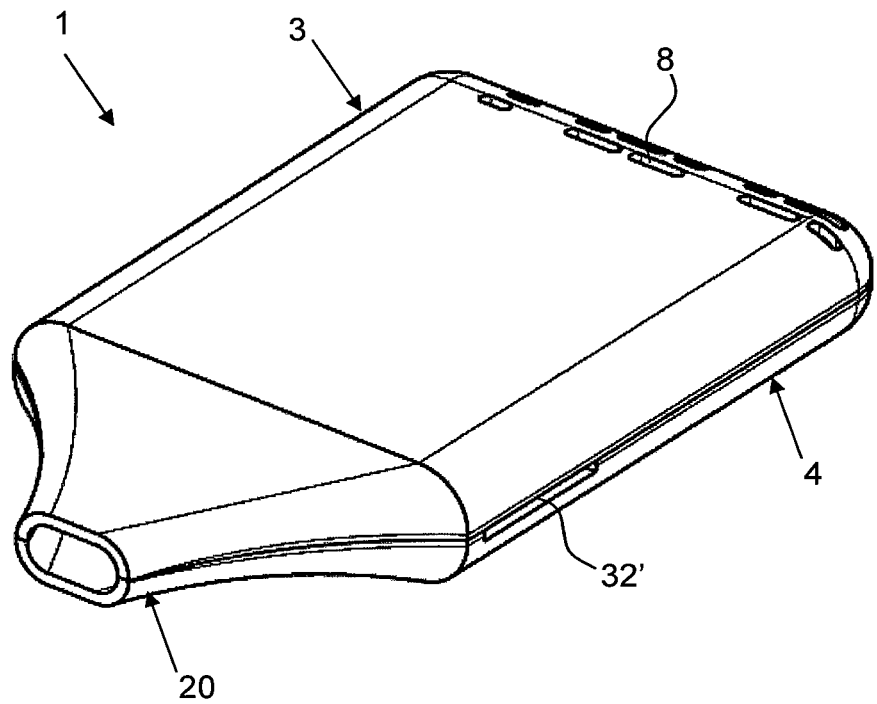
FIG. 9 a perspective plan view of the powder inhaler according to the invention in closed state with mouthpiece as outlet.
Figure 10:
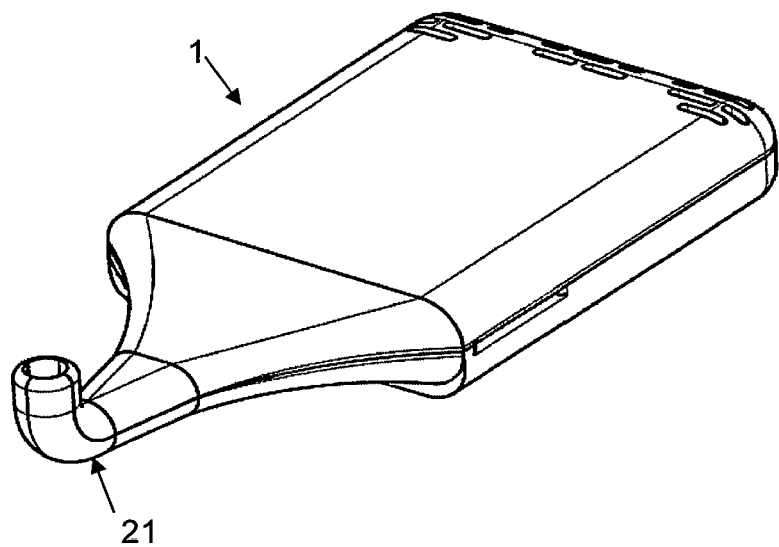
FIG. 10 a perspective plan view of a powder inhaler according to the invention in closed state with nose piece as outlet.

FIG. 9 shows a powder inhaler 1 in the folded closed state in which the outlet is formed as a spout 20 as in FIGS. 1 to 8. Generally, it is however conceivable for both embodiments of the powder inhaler 1 to form the outlet as a nose tube 21, as illustrated in FIG. 10.

All powder inhalers 1 according to the invention can be divided roughly into three partial areas:
- the air supply area which extends from the back wall 31 provided with air inlets 8, i.e., the wall present on the base of the half shell 3 and facing away from the outlet area, all the way to the blister chamber 11 and which comprises the funnel-shaped air supply channel provided with the air swirling structure 5 and delimited by the guide webs 6, and
- the powder deposition and release area which comprises the blister chamber 11 with the powder receiving depression 9 in which active ingredient depression 101 of a blister element 100 can be received;

the outlet area with respective de-agglomeration structures 17, 17' and a formed mouthpiece or nose piece.

The configuration according to the invention of the three partial areas ensures that, upon inhalation, an optimal air stream for delivery of the active ingredient, in the following also referred to as medicament, is generated, independent of the way the patient is inhaling. In this way, the medicament can be optimally inhaled and thereby best possible effect achieved.

The air supply area in the embodiments illustrated in the figures is formed by the air supply channel which is delimited by the guide webs 6 and is tapering toward the powder receiving depression 9 into which air is flowing in through the air inlets 8 when the patient breathes in with the mouth piece 20 received in the mouth. The air inlets 8 are provided in the back wall 31 of the half shell 3 as well as at the contact surface of the back walls 31, 41 between both half shells 3, 4 (compare FIG. 5). The tapering air supply channel and the air swirling structure 5 respectively arranged therein cause turbulence and increase the speed of the air supply stream prior to entry into the powder receiving depression 9.

Of course, the number of air supply channels and air swirling structures which are arranged therein in other embodiments, in particular also in embodiments with more than one powder receiving depression, can be varied by appropriate increase of the number of guide webs.

For arranging the blister 100 (compare FIG. 2.), the half shell 4 in one sidewall 42 has a cutout 32' through which the inserted blister 100 with folded over pulling tab 102 of the cover film of the blister element 100 is extending. This cutout 32' is air-tightly closed by the projection 32" at the other half shell 3. The active ingredient depression 101 of the blister 100 which can also be referred to as a capsule is received in the depression 9 which is formed in the half shell 4. For position-precise arrangement of the blister 100, stops 12 are moreover provided in the half shell 4.

For securing the blister element 100 so as to be immobile in the powder inhaler 1 when, for opening the active ingredient depression 101, one pulls on the section 102 of the cover film of the blister element 100 projecting out of the powder inhaler 1, the end of the support plate of the blister element 100 which is facing away therefrom is received between the sidewall sections 32, 42 of the half shells 3, 4 opposite the cutout 32' and the projection 32". For this purpose, this section of the sidewalls 32, 42 is provided with ribbing 18.

For guiding the air stream through the inserted, open active ingredient depression 101, at appropriate location in the half shell 3, on both sides of the powder receiving depression 9 or the active ingredient depression 101, guide walls 7 are arranged (FIG. 1, FIG. 7) which extend away from the longitudinal webs 6 and guide the airstream out of the air inlet area through the powder receiving depression 9 or the open depression 101 of the blister element 100 arranged therein and filled with powder.

The blister chamber 11 is adjoined by the outlet area through which the now formed aerosol of air and medicament powder is released. The blister chamber 11 in the outlet area is delimited by the de-agglomeration structures 17, 17' by means of which the air stream, now laden with the active ingredient, cannot directly reach the outlet but, due to the further deflection, turbulences are generated in order to prevent deposition or agglomeration of the powder medicament. However, downstream of the passage through the powder receiving depression 9 narrowly delimited by the guide walls 7, a cross-sectional widening initially causes a reduction of the flow speed and creates in this way a spacer effect, i.e., the active ingredient particles are distributed uniformly within the air stream. The de-agglomeration of the active ingredient particles is subsequently enhanced on the other hand by the de-agglomeration structures 17, 17' in the outlet end that is tapering by means of the wall sections 22 and provided with mouthpiece 20.

In the figures, the powder inhalers 1 each have three de-agglomeration structures 17, 17' wherein in the embodiment in FIGS. 1 to 4 a de-agglomeration structure 17 is arranged in the lower half shell 4 and two de-agglomeration structures 17 in the upper half shell 3. Generally, it is however also possible to provide more or fewer de-agglomeration structures; also, they can all be provided in one of the half shell or distributed differently on the two half shells.

The or each de-agglomeration structure 17, 17' in the outlet area can be formed by a group of profiled elements, e.g. lamellas, that are arranged in a ring shape about a cylinder. These lamellas can have an airfoil-like profile in order to impart defined turbulence to the air stream.

In the embodiment according to FIGS. 5 to 7, the three de-agglomeration structures are each formed by two half structures 17' in each of the half shells 3, 4. The half structures 17' extend only to the partition plane defined by the half shells 3, 4 so that they can be pivoted about the pivot joint 15 and cutout 15'. Generally, in this embodiment care must taken that none of the elements and structures in the interior of the half shells 3, 4, also the guide walls 7 and the transverse stays 53, project past the partition plane. For this reason, the sidewall 32 of the half shell 3 also does not have a projection relative to the cutout 32' at the sidewall 42 of the half shell 4; the cutout 32' is therefore designed with a reduced depth so that the half shells 3, 4 seal tightly at this location with inserted blister element. Only the section of the sidewall 32 or half shell 3 with ribbing 18 projects past the partition plane and the corresponding section with the ribbing 18 at the sidewall 42 of the lower half shell 4 is appropriately lowered.

This arrangement is associated with pivoting of the upper half shell 3 for opening in clockwise direction and for closing in counterclockwise direction. If the ribbed projection were provided at the lower half shell and an appropriately lowered ribbed section at the upper half shell, the pivot directions for opening and closing would be exactly reversed. In order to make the use of the device easy for the user, appropriate information, for example, markings by arrows, can be provided on the exterior side of the half shells.

A powder inhaler 1 comprised of two half shells 3 and 4 according to the invention can advantageously be produced quickly and inexpensively by injection molding of a plastic material. All required structures are positioned in the half shells or, in case of the truncated cone shaped spiral, are formed as one piece with one of the half shells. The assembly of the half shells at the longitudinal hinge or the pivot joint is not complicated; no further individual parts are required.

Advantageously, the powder inhaler 1 of two half shells 3, 4, after insertion of a blister element 100 in the open state, can be easily transferred by folding or pivoting into the ready to use state. Due to the flat configuration, the powder inhaler 1 can be carried along in a simple and comfortable way without pockets of clothing being excessively bulged. When administration of the medicament is required, it is only necessary to pull off the end section 102 for opening the powder depression 101 and the medicament can be inhaled.

As can be seen in FIGS. 1 to 4, moreover an additional or alternative opening mechanisms for the active ingredient depression 101 of a blister element 100 can be provided which comprises a plunger 10 that is designed as a pricker. The pricker 10 is secured in the half shell 3 by an elastic insert 14 which has a curvature 14' in outward direction (see FIG. 4) and which indicates to the user the pressure point that must be actuated in order to penetrate an inserted blister depression 101 with the pricker 10. After actuation of the pressure point by the user, the pricker 10 is returned again by the elastic insert 14 into its initial position and deflects moreover the air stream into the powder receiving depression or the active ingredient depression. The manufacture of this powder inhaler can be realized in that first the elastic insert 14 is injection molded and the remaining inhaler shape is injection molded onto the elastic insert 14, or vice versa, for example, by a 2C injection molding method. Of course, a powder inhaler with longitudinal hinge and insertable air swirling structure can also be formed without plunger so that opening of the active ingredient depression is realized only by pulling off the pulling tab of the cover film of the blister element that is projecting out off the powder inhaler.

Figure 4:
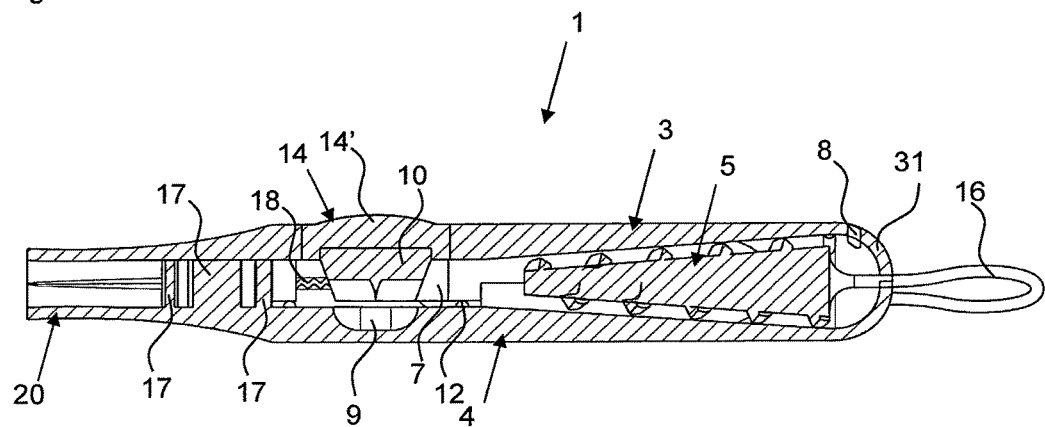
Figure 5:
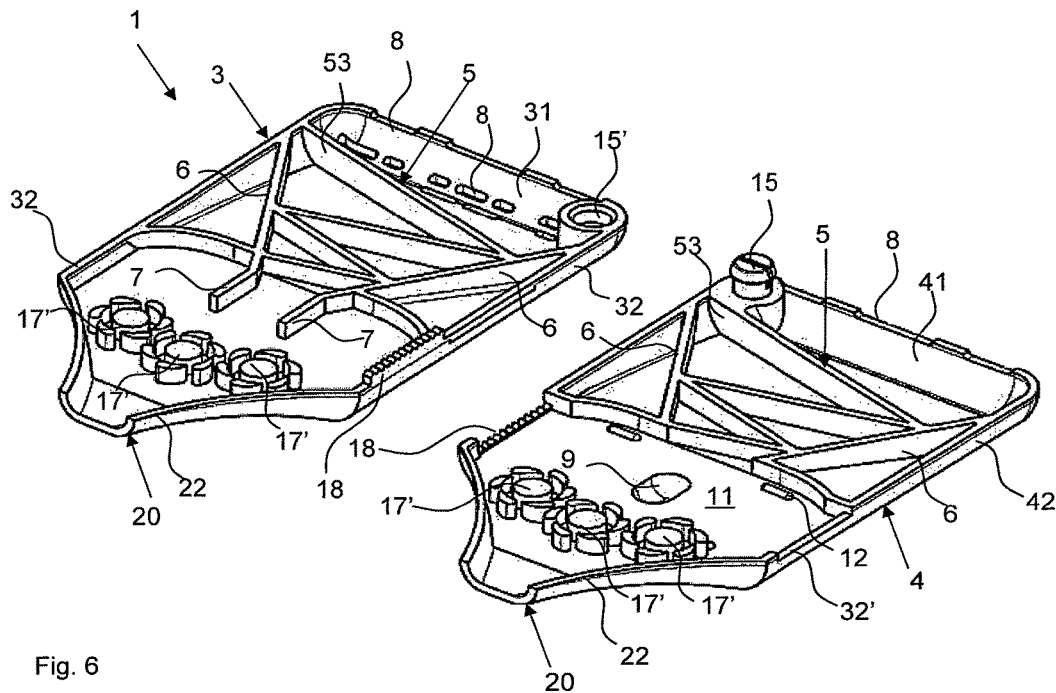
FIG. 5 a perspective view of the two half shells of a further powder inhaler according to the invention with pivot joint connection.
Figure 6:
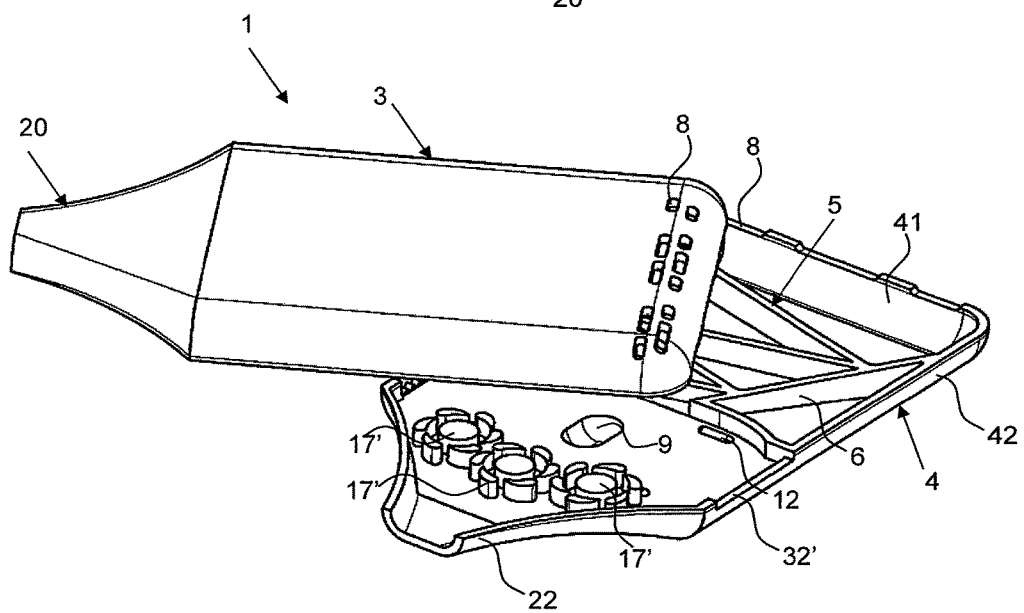
FIG. 6 a perspective view of the powder inhaler with two half shells of FIG. 5 in half-open position.
Figure 7:
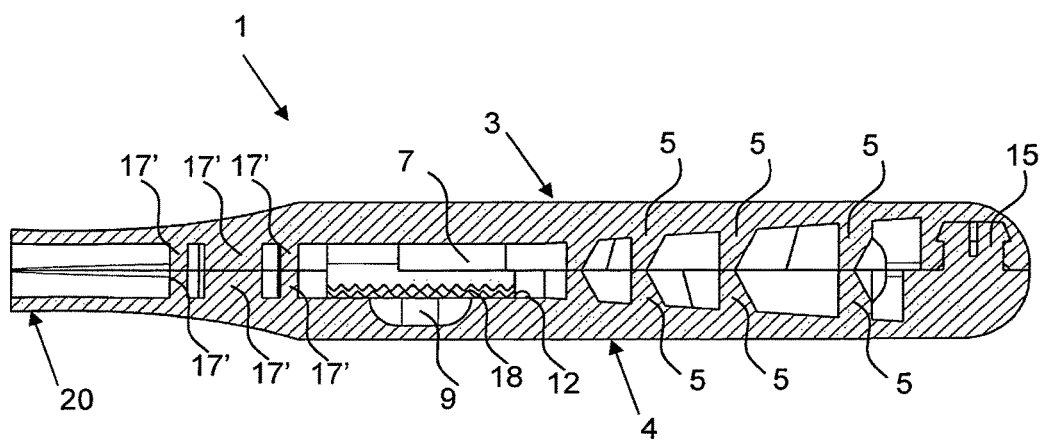
FIG. 7 a longitudinal section view of the powder inhaler of FIG. 6 in closed state without blister.
Figure 8:
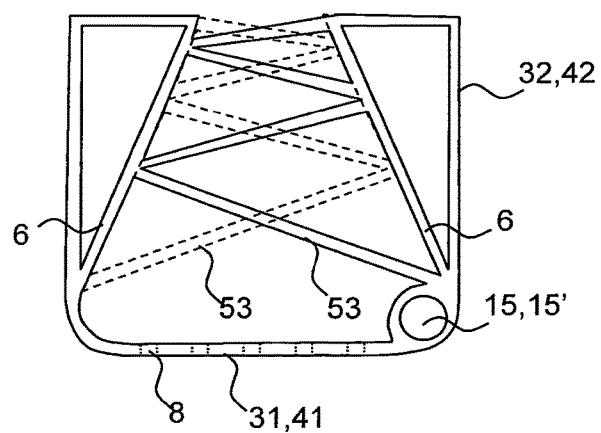
FIG. 8 schematic plan view of the air swirling structure of transverse stays of the powder inhaler of FIGS. 6/7.

Moreover, FIG. 4 shows in longitudinal section view that the air supply channel not only tapers in regard to width but also to height in the direction toward the blister chamber 11 wherein the wall thickness of the half shells 3 and 4 is increased at the same time. The air stream which is entering through the air inlets 8 is caused to rotate (similar to a tornado) along the coil-shaped or spiral-shaped path that is predetermined by the air swirling structure 5. By rotation centrifugal forces and pressure phenomena are generated which are important for the complete entrainment of the powder out of the powder receiving depression 9.

| List of Reference Numerals | |
|---|---|
| 1 | powder inhaler |
| 3 | first half shell |
| 4 | second half shell |
| 5 | air swirling structure |
| 6 | guide web |
| 7 | guide wall |
| 8 | air inlet opening |
| 9 | powder receiving depression |
| 10 | plunger |
| 11 | blister chamber |
| 12 | stop |
| 14, 14' | elastic insert with pressure dome |
| 15, 15' | pivot joint |
| 15" | longitudinal hinge |
| 16 | film hinge |
| 17 | de-agglomeration structure |
| 17' | half structure |
| 18 | ribbing |
| 20 | mouthpiece |
| 21 | nose tube |
| 22 | outlet wall |
| 31, 41 | back wall of the half shells |
| 32, 42 | sidewall of the half shells |
| 32' | cutout |
| 32" | projection |
| 51 | elliptical truncated cone |
| 52 | spiral-shaped projection |
| 53 | transverse stay |
| 100 | blister |
| 101 | active ingredient depression |
| 102 | folded over pulling tab of the cover film |

What is claimed is:

1. A powder inhaler (1), comprising:
   two flat, elongate half shells (3, 4) connectable or connected to each other by an articulated connection and, in a joined arrangement of the half shells, enclosing an air inlet area, a powder deposition and release area, and an outlet area through which a fluid path is extending, wherein the half shells (3, 4) each are rimmed by sidewalls (32, 42) and a wall section (31, 41) opposite the outlet area;

wherein, in the air inlet area, at least one of the half shells (3, 4) comprises at least one air inlet opening (8), which is arranged on the wall section (31, 41), and wherein at least one air supply channel delimited by guide webs (6) extends from the at least one air inlet opening (8) to the powder deposition and release area, wherein the at least one air supply channel has a cross-section that is tapering in a direction toward the powder deposition and release area, and wherein the at least one air supply channel defines the fluid path between the at least one air inlet opening (8) and the powder deposition and release area;

wherein at least one air swirling structure (5) is disposed in the at least one air supply channel;

wherein, in the powder deposition and release area, one of the half shells (3, 4) comprises at least one powder receiving depression (9) for receiving an active ingredient depression (101) of a blister element (100), wherein guide walls (7) are provided that, in the joined arrangement, frame the at least one powder receiving depression (9) along the fluid path on two sides and extend away from outermost guide webs (6) extending to the at least one powder depression (9);

wherein a cross-section of the fluid path between the powder deposition and release area and the outlet area widens downstream of a passage through the powder receiving depression (9) delimited by the guide walls (7);

wherein the outlet area has a tapering outlet end and an outlet for aerosol is formed by the half shells, wherein the outlet area comprises one or more de-agglomeration structures (17, 17');

wherein, for opening an active ingredient depression (101) of a blister element (100) inserted into the powder inhaler (1), a pricker is provided that is elastically supported in the powder inhaler relative to the at least one powder receiving depression (9) and/or the sidewalls (32, 42) of the half shells (3, 4) delimit between them an opening at the level of the at least one powder receiving depression (9) in the joined arrangement of the half shells (3, 4), wherein, when a blister element (100) is inserted into the powder inhaler, a cover plate that closes off an active ingredient depression (101) of the blister element (100) is projecting outwardly from the opening.

2. The powder inhaler (1) according to claim 1, wherein the half shells (3, 4) comprise a substantially rectangular, trapezoidal, drop-shaped or oval base rimmed by the sidewalls (32, 42) and the wall section (31, 41), and wherein the guide webs (6), provided on at least one of the half shells (3, 4) and extending from the wall section (31, 41) and/or from the sidewalls (32, 42) neighboring the wall section (31, 41) all the way to the at least one powder receiving depression (9), have a height extending all the way to the other half shell (3, 4) or all the way to the guide webs (6) of the other half shell (3, 4) for forming the at least one air supply channel, wherein two side by side neighboring guide webs (6) form an air supply channel, respectively.

3. The powder inhaler (1) according to claim 1, further comprising at least two powder receiving depressions (9), wherein at least one air inlet channel extends to each one of the powder receiving depressions (9), respectively.

4. The powder inhaler (1) according to claim 1, wherein the air swirling structure (5) is formed by an elliptical truncated cone (51) to be arranged in the at least one air supply channel between the guide webs (6) that are neighboring each other and comprising at least one projection (52) that extends in a spiral shape along a wall surface of the elliptical truncated cone (51), or several transverse stays (53) that extend between the guide webs (6) that are neighboring each other, wherein the transverse stays (53) are arranged in both half shells (3, 4) such that in the joined arrangement they extend oppositely oriented relative to each other.

5. The powder inhaler (1) according to claim 4, wherein the truncated cone (51) comprises a base surface and is connected by the base surface to the wall section (31, 41) of one of the half shells (3, 4).

6. The powder inhaler (1) according to claim 4, wherein the elliptical truncated cone (51) is connected by at least one film hinge (16) to the wall section (31, 41) of one of the half shells (3, 4).

7. The powder inhaler (1) according to claim 1, wherein the articulated connection of the half shells (3, 4) is a hinge (15") connecting the sidewalls (32, 42) on one side of the half shells or is a pivot joint (15, 15').

8. The powder inhaler (1) according to claim 7, wherein the pivot joint (15, 15') is arranged in an area between one of the sidewalls (32, 42) and the wall section (31, 41).

9. The powder inhaler (1) according to claim 1, wherein the one or more de-agglomeration structures (17) are formed by a group of profiled elements arranged in a ring shape about a full cylinder structure that extends between the two half shells (3, 4), wherein the one or more de-agglomeration structures (17) are arranged on one of the half shells (3, 4) or several of the de-agglomeration structures (17) are distributed at different locations in the outlet area on each one of the half shells (3, 4), or the one or more de-agglomeration structures (17) are formed by two half structures (17'), respectively, and one of the half structures (17') is arranged on each half shell (3, 4), respectively, so that the half structures (17') in the joined arrangement of the half shells (3, 4) form the one or more de-agglomeration structures (17) extending between the two half shells (3, 4).

10. The powder inhaler (1) according to claim 1, further comprising an elastic insert (14), wherein the pricker is a plunger (10) connected to the elastic insert (14), wherein the elastic insert (14) with the plunger (10) is arranged in the half shell (3, 4) without the at least one powder receiving depression (9) in the powder deposition and release area at a location which is positioned opposite the at least one powder receiving depression (9), and the plunger (10) is moveable by the elastic insert (14) in the direction toward the at least one powder receiving depression (9).

11. The powder inhaler (1) according to claim 1, wherein the opening is formed by a cutout (32') on the sidewall of a first one of the half shells (3, 4) at the level of the powder receiving depression (9), wherein a width and a height of the cutout corresponds to a width and a height of a blister element (100) dimensioned for reception into the powder inhaler (1), wherein a second one of the half shells (3, 4) comprises a projection (32") on the sidewall (42) that, in a joined arrangement of the half shells (3, 4), is positioned above the cutout (32'), wherein the projection (32") is designed to close off the cutout (32') when a blister element (100) is received in the powder inhaler (1).

12. The powder inhaler (1) according to claim 11, wherein the sidewalls (32, 42) of the half shells (3, 4) arranged opposite the cutout (32') and opposite the projection (32") comprise a ribbing (18) at the level of the powder receiving depression (9), wherein a width of the ribbing corresponding to a width of a blister element (100) dimensioned for reception in the powder inhaler (1).

13. The powder inhaler (1) according to claim 11, wherein the first half shell (3, 4) comprises a projection that is designed to engage a corresponding cutout (103) of the blister element (100) dimensioned for reception in the powder inhaler (1).

14. The powder inhaler (1) according to claim 13, wherein the projection is a dome-shape projection.

15. The powder inhaler (1) according to claim 11, wherein the first half shell (3, 4) comprise at least one stop (12) arranged for framing a blister element (100) when inserted in the powder inhaler (1).

16. The powder inhaler (1) according to claim 1, wherein the half shells (3, 4, 15) comprise locking means for releasably joining the half shells (3, 4).

17. A powder inhalation set (1, 100) comprising a powder inhaler (1) according to claim 11 and a blister element (100) dimensioned for reception in the powder inhaler (1), wherein the blister element (100) comprises a support film with at least one depression (101) that is formed for receiving at least one active ingredient powder that is inhalable, and a cover plate that closes off the depression (101), wherein the at least one depression (101) of the blister element (100) in size and position is formed to be received in a powder receiving depression (9) of the powder inhaler (1).

18. The powder inhalation set (1, 100) according to claim 17, wherein, for opening the depression (101), the cover plate is designed to be removable from the support plate through the opening at the level of the powder receiving depression (9) of the powder inhaler (1), and/or the cover plate is penetrable by the pricker embodied as a plunger (10), which is arranged opposite the powder receiving depression (9) and is elastically moveable.

\* \* \* \* \*